(12) United States Patent
Badylak

(10) Patent No.: US 8,084,048 B2
(45) Date of Patent: Dec. 27, 2011

(54) VASCULARIZATION ENHANCED GRAFT CONSTRUCTS

(75) Inventor: Stephen F. Badylak, Pittsburgh, PA (US)

(73) Assignee: Purdue Research Foundation, West Lafayette, IN (US)

( * ) Notice: Subject to any disclaimer, the term of this patent is extended or adjusted under 35 U.S.C. 154(b) by 302 days.

(21) Appl. No.: 12/557,176

(22) Filed: Sep. 10, 2009

(65) Prior Publication Data

US 2009/0324681 A1    Dec. 31, 2009

Related U.S. Application Data

(62) Division of application No. 10/428,355, filed on May 2, 2003, now Pat. No. 7,795,022.

(60) Provisional application No. 60/377,565, filed on May 2, 2002.

(51) Int. Cl.
*A61K 35/407*   (2006.01)
*A61K 35/12*    (2006.01)

(52) U.S. Cl. ........ 424/400; 424/422; 424/572; 435/325; 435/371

(58) Field of Classification Search .................. 424/400, 424/422, 572; 435/325, 371
See application file for complete search history.

(56) References Cited

U.S. PATENT DOCUMENTS

| | | | |
|---|---|---|---|
| 4,829,000 A | 5/1989 | Kleinman et al. | |
| 4,883,864 A | 11/1989 | Scholz | |
| 4,902,508 A | 2/1990 | Badylak et al. | |
| 4,956,178 A | 9/1990 | Badylak et al. | |
| 5,108,424 A | 4/1992 | Hoffman et al. | |
| 5,275,826 A | 1/1994 | Badylak et al. | |
| 5,281,422 A | 1/1994 | Badylak et al. | |
| 5,352,463 A | 10/1994 | Badylak et al. | |
| 5,554,389 A | 9/1996 | Badylak et al. | |
| 5,641,518 A | 6/1997 | Badylak et al. | |
| 5,814,328 A | 9/1998 | Gunasekaran | |
| 5,863,531 A | 1/1999 | Naughton et al. | |
| 5,885,619 A | 3/1999 | Patel et al. | |
| 5,945,101 A | 8/1999 | Berg et al. | |
| 5,955,110 A | 9/1999 | Patel et al. | |
| 6,022,743 A | 2/2000 | Naughton et al. | |
| 6,099,567 A | 8/2000 | Badylak et al. | |
| 6,127,143 A | 10/2000 | Gunasekaran | |
| 6,171,344 B1 | 1/2001 | Atala | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,264,992 B1 | 7/2001 | Voytik-Harbin et al. | |
| 6,358,284 B1 | 3/2002 | Fearnot et al. | |
| 6,375,989 B1 | 4/2002 | Badylak et al. | |
| 6,379,710 B1 | 4/2002 | Badylak | |
| 6,419,920 B1 | 7/2002 | Mineau-Hanschke et al. | |
| 6,475,232 B1 | 11/2002 | Babbs et al. | |
| 6,485,723 B1 | 11/2002 | Badylak et al. | |
| 6,918,396 B1 | 7/2005 | Badylak et al. | |
| 6,962,814 B2 | 11/2005 | Mitchell et al. | |
| 7,087,089 B2 | 8/2006 | Patel et al. | |
| 7,175,841 B2 | 2/2007 | Badylak et al. | |
| 7,771,717 B2 | 8/2010 | Badylak et al. | |
| 7,776,596 B2 | 8/2010 | Badylak | |
| 7,795,022 B2 | 9/2010 | Badylak | |
| 7,815,686 B2 | 10/2010 | Badylak | |
| 2003/0113302 A1 | 6/2003 | Revazova et al. | |
| 2005/0202058 A1 | 9/2005 | Hiles et al. | |
| 2006/0257377 A1 | 11/2006 | Atala et al. | |

FOREIGN PATENT DOCUMENTS

| | | |
|---|---|---|
| JP | 2000-516503 | 12/2000 |
| WO | WO 98/06445 | 2/1998 |
| WO | WO 98/25637 | 6/1998 |
| WO | WO 00/15765 A1 | 3/2000 |
| WO | WO 00/62833 A1 | 10/2000 |
| WO | WO 01/10355 | 2/2001 |
| WO | WO 01/45765 | 6/2001 |
| WO | WO 01/48153 A1 | 7/2001 |
| WO | WO 01/78754 | 10/2001 |
| WO | WO 02/07646 A2 | 1/2002 |
| WO | WO 02/14480 A2 | 2/2002 |
| WO | WO 02/20729 A2 | 3/2002 |

OTHER PUBLICATIONS

Nugent et al., "Endothelial Implants Inhibit Intimal Hyperplasia After Porcine Angioplasty," *Circulation Research*, Mar. 5, 1999, vol. 84, No. 4, p. 384-391.

Voytik-Harbin et al., "Three-Dimensional Imaging of Extracellular Matrix and Extracellular Matrix-Cell Interactions," Methods in Cell Biology, Ch. 27, vol. 43, pp. 583-597.

Brightman et al., "Time-Lapse Confocal Reflection Microscopy of Collagen Fibrillogenesis and Extracellular Matrix Assembly In Vitro," *Biopolymers*, vol. 54, 2000, pp. 222-234.

(Continued)

*Primary Examiner* — Ruth Davis
(74) *Attorney, Agent, or Firm* — Barnes & Thornburg LLP

(57) ABSTRACT

A tissue graft construct for use in repairing diseased or damaged tissues is provided. The tissue graft construct comprises a matrix composition selected from the group consisting of liver basement membrane and extracts and hydrolysates thereof, and processed collagen from vertebrate non-submucosal sources, added endothelial cells, and at least one additional preselected, exogenous population of cells which enhance the initiation of vessel-like structures in the grant. The preselected population of cells can be a population of non-keratinized or keratinized epithelial cells or a population of mesodermally derived cells selected from the group consisting of fibroblasts, smooth muscle cells, skeletal muscle cells, cardiac muscle cells, multi-potential progenitor cells, pericytes, osteogenic cells, and any other suitable cell type, preferably selected based on the tissue to be repaired. Methods for enhancing the vascularization in vivo of these tissue graft constructs and for preparing these graft constructs are also provided.

22 Claims, 1 Drawing Sheet

OTHER PUBLICATIONS

Asem et al., "Basal Lamina of Avian Ovarian Follicle: Influence on Morphology of Granulosa Cells In-Vitro," *Comparative Biochemistry and Physiology, Part C*, 125 (2000), pp. 189-201.

Asem et al., "Effect of Basal Lamina on Progesterone Production by Chicken Granulosa Cells In Vitro—Influence of Follicular Development," *Comparative Biochemistry and Physiology, Part C*, 125 (2000), pp. 233-244.

Hirschi et al., "PDGF TGF-β, and Heterotypic Cell-Cell Interactions Mediate Endothelial Cell-Induced Recruitment of 10T1/2 Cells and Their Differentiation to a Smooth Muscle Fate." *The Journal of Cell Biology*, vol. 141, No. 3, May 4, 1998, pp. 805-814.

Campbell et al., "Endothelial Cell Influences on Vascular Smooth Muscle Phenotype." *Ann. Rev. Physiol.*, 1986, vol. 48, pp. 295-306.

Badylak et al., "Endothelial cell adherence to small intestinal submucosa: an acellular bioscaffold," *Biomaterials*, vol. 20, 1999, pp. 2257-2263.

Castano. E., et al., "Inhibition of DNA Synthesis by Aspirin in Swiss 3T3 Fibroblasts," Journal of Pharmacology and Experimental Therapeutics. vol. 280, No. 1, 1997, pp. 366-372.

Bhatia, S. N., et al., "Controlling Cell Interactions by Micropatterning in Co-Cultures: Hepatocytes and 3T3 Fibroblasts," Journal of Biomedical Materials Research, vol. 34, 1997, pp. 189-199.

Liu, C. H., et al., "Effects of Salvianolic Acid-A on NIH/3T3 Fibroblast Proliferation. Collagen Synthesis and Gene Expression," World J. Gastroentero, vol. 6, No. 3. 2000, pp. 361-364.

Keyes. K,. et al., "An In Vitro Tumor Model: Analysis of Angiogenic Factor Expression after Chemotherapy," Cancer Research, vol. 62, 2002, pp. 5597-5602.

Montesano, R., "Paracrine Induction of Angiogenesis in Vitro by Swiss 3T3 Fibroblasts" Journal of Cell Science, vol. 105, 1993, pp. 1013-1024.

Nerem, R., "Tissue Engineering: The Hope, The Hype and The Future" Tissue Engineering, vol. 12, No. 5, 2006, p. 1143-1150.

"Artificial Blood Vessel", English translation of Japanese Patent Application Publication No. 3-12169, 1991, 16 pages.

"In Vivo Plant Material". English translation of Japanese Patent Application Publication No. 1-170466, 1989, 13 pages.

Ho. M., et al.. "Identification of Engothelial Cell Genes by Combined Database Mining and Microarray Analysis", Physiol Genomics, vol. 13, 2003, pp. 249-262.

Maru, Y. et al., "An Oncogenic Form of the Flt-1 Kinase has a Tubulogenic Potential in a Sinusoidal Endothelial Cell Line," European Journal of Cell Biology, vol. 79, 2000, pp. 130-143.

Russmann H. et al., "Translocation of *Yersinia enterocolitica* through an Endothelial Monolayer by Polymorphonuclear Leukocytes," Infection and Immunity, vol. 64, No. 3, 1996, pp. 1016-1019.

Kubota Y. et al., "Role of Laminin and Basement Membrane in the Morphological Differentiation of Human Endothelial Cells into Capillary-like Structures," Journal of Cell Biology, vol. 107, 1988, pp. 1589-1598.

Block, S., "Peroxygen Compounds," Disinfection, Sterilization and Preservation, 4th Edition 1991, pp. 167-181. Philadelphia, Lea & Febiger.

Denton. G.W., "Chlorhexidine," Disinfection, Sterilization and Preservation, S.Block, editor, 4th Edition 1991, pp. 274-289. Philadelphia, Lea & Febiger.

Yang et al., "Tissue engineered artificial skin composed of dermis and epidermis," Artificial Organ, 2000; 24(1):7-17.

Lim et al., "Microencapsulated Islets as Bioartificial Endocrine Pancreas," Science, 1980, 210(4472):908-10.

U.S. Appl. No. 12/852,897, filed Aug. 9, 2010, Badylak et al.

VASCULARIZATION ENHANCED GRAFT CONSTRUCTS

CROSS-REFERENCE TO RELATED APPLICATION

This application is a divisional application of U.S. patent application Ser. No. 10/428,355, filed May 2, 2003, which claims priority under 35 U.S.C. §119(e) to U.S. Provisional Application No. 60/377,565, filed May 2, 2002.

GOVERNMENT RIGHTS

This invention was made with government support under Grant No. GM60691-01 awarded by the National Institutes of Health. The government has certain rights in the invention.

FIELD OF THE INVENTION

The preset invention relates to vascularization enhanced tissue grafts derived from a matrix composition and their use in repairing diseased or damaged tissues. More particularly, this invention is directed to vascularization enhanced tissue grafts comprising a matrix composition that has been seeded with endothelial cells and at least one additional preselected, exogenous population of cells to enhance the repair capabilities of the tissue graft constructs.

BACKGROUND AND SUMMARY OF THE INVENTION

The present invention is directed to a tissue graft construct comprising a matrix composition seeded with endothelial cells and at least one additional preselected, exogenous cell population for use in the repair of damaged or diseased tissues. The matrix composition for use in accordance with the present invention is selected from the group consisting of liver basement membrane and extracts and hydrolysates thereof, and processed collagen from vertebrate non-submucosal sources. The matrix composition preferably comprises highly conserved collagens, glycoproteins, proteoglycans, and glycosaminoglycans. The matrix composition for use in this invention is derived from the tissue of a warm-blooded vertebrate.

The tissue graft constructs prepared in accordance with the present invention are substantially acellular matrices that provide a superior cell growth substrate resembling the matrix environment found in vivo. The natural composition and configuration of the matrix composition provides a unique cell growth substrate that promotes the attachment and proliferation of cells in vitro and induces tissue remodeling when the graft constructs are implanted in vivo.

As tissue graft materials, liver basement membrane and extracts and hydrolysates thereof, and processed collagen from vertebrate non-submucosal sources, induce the growth of endogenous tissues upon implantation into a host (i.e., the graft materials induce remodeling). When used in such an application the tissue graft constructs appear not only to serve as a matrix for the growth or regrowth of the tissues replaced by the graft constructs, but also to promote or to induce such growth or regrowth of endogenous tissue. These graft materials can be used in an implantable sheet form or in injectable fluidized or gel forms for inducing the regrowth of endogenous tissues.

The present invention is directed to tissue graft constructs comprising a matrix composition selected from the group consisting of liver basement membrane and extracts and hydrolysates thereof, and processed collagen from vertebrate non-submucosal sources, and further including added endothelial cells and at least one additional preselected, exogenous population of cells. The invention is also directed to methods of enhancing the vascularization of a tissue graft construct in vivo. The vascularization enhanced tissue graft constructs are prepared by seeding the matrix composition in vitro with endothelial cells or endothelial cell precursors (e.g., progenitor cells or stem cells) and at least one additional preselected or predetermined cell type prior to implanting or injecting the tissue graft construct into the host.

One embodiment provides a tissue graft construct for use in repairing diseased or damaged tissues. The tissue graft construct comprises a matrix composition selected from the group consisting of liver basement membrane and extracts and hydrolysates thereof, and processed collagen from vertebrate non-submucosal sources, added endothelial cells, and at least one additional preselected, exogenous population of cells.

In another embodiment a vascularized tissue graft construct is provided for use in repairing diseased or damaged tissues. The tissue graft construct comprises a matrix composition selected from the group consisting of liver basement membrane and extracts and hydrolysates thereof, and processed collagen from vertebrate non-submucosal sources, added endothelial cells, and at least one additional preselected, exogenous population of cells wherein the endothelial cells have been cultured on the matrix composition for a time sufficient to form vessels or vessel-like structures in vitro.

In another embodiment a method is provided for enhancing the vascularization in vivo of a tissue graft construct. The method comprises the steps of seeding in vitro a matrix composition selected from the group consisting of liver basement membrane and extracts and hydrolysates thereof, and processed collagen from vertebrate non-submucosal sources, with a population of endothelial cells and at least one additional preselected, exogenous population of cells to form the graft construct, and implanting the graft construct into a vertebrate at a site in need of repair.

In yet another embodiment a method is provided for enhancing the vascularization in vivo of a tissue graft construct. The method comprises the steps of seeding in vitro a matrix composition selected from the group consisting of liver basement membrane and extracts and hydrolysates thereof, and processed collagen from vertebrate non-submucosal sources, with a population of endothelial cells and at least one additional preselected, exogenous population of cells, culturing in vitro the endothelial cells for a time sufficient to induce the formation of vessels or vessel-like structures or components, and implanting the graft construct into a vertebrate in a site in need of repair.

In either of these method embodiments the matrix composition can be seeded with the additional preselected population of cells after the matrix composition is seeded with the endothelial cells, the matrix composition can be seeded with the additional preselected population of cells before the matrix composition is seeded with the endothelial cells, or the matrix composition can be seeded with the endothelial cells and the additional preselected population of cells simultaneously or nearly simultaneously.

The endothelial cells can be cultured in vitro on the matrix composition for a time sufficient to induce the formation of vessels or vessel-like structures, or the endothelial cells can be cultured on the matrix composition for a time sufficient to expand the endothelial cells (i.e., allow the endothelial cells to divide at least one time) without forming vessels or vessel-like structures in vitro. Alternatively, the graft construct can be implanted without expanding the endothelial cells. In any of these embodiments the additional preselected population of cells may or may not be expanded (i.e., allowed to progress through at least one cell division cycle) prior to implanting the graft construct.

In still another embodiment a method is provided of preparing a tissue graft construct for use in repairing diseased or damaged tissues. The method comprises the step of seeding in vitro a matrix composition selected from the group consisting of liver basement membrane and extracts and hydrolysates thereof, and processed collagen from vertebrate non-submucosal sources, with a population of endothelial cells, and at least one additional preselected, exogenous population of cells to form the graft construct. The method can further comprise the step of culturing the endothelial cells in vitro on the matrix composition for a time sufficient to induce the formation of vessels or vessel-like structures.

In any of these embodiments the at least one additional cell population can comprise a population of non-keratinized or keratinized epithelial cells or a population of mesodermally derived cells selected from the group consisting of fibroblasts, smooth muscle cells, skeletal muscle cells, cardiac muscle cells, multi-potential progenitor cells (e.g., stem cells), pericytes, and osteogenic cells. In various embodiments, the matrix composition can be seeded with endothelial cells and one or more of these additional cell types (i.e., the matrix composition can be seeded with endothelial cells and one, two, three, etc. of these additional cell types).

DETAILED DESCRIPTION OF THE INVENTION

Figure 1:
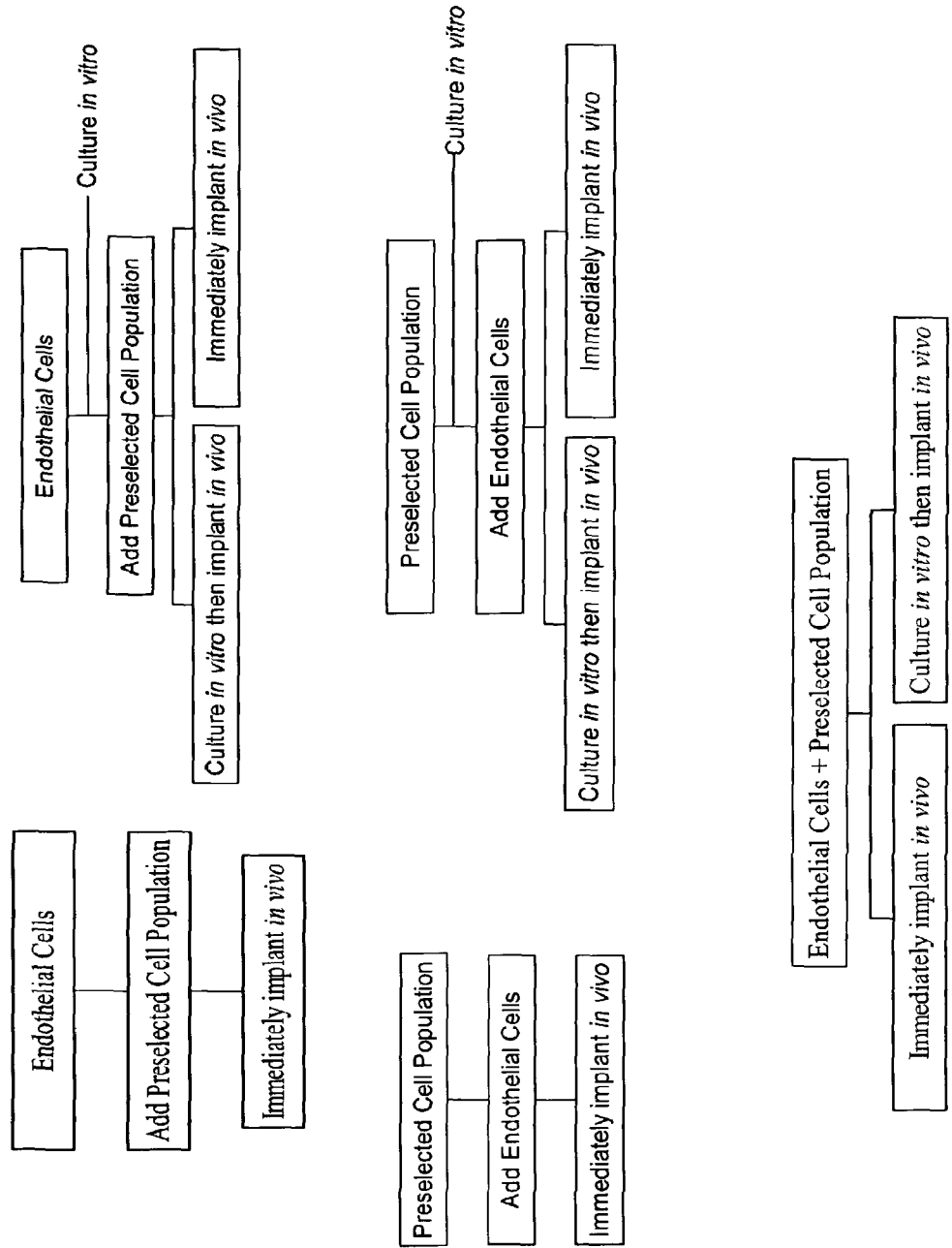
FIG. 1 provides flow charts depicting alternative preparations of the present graft constructs.

The present invention is directed to a tissue graft construct comprising a matrix composition selected from the group consisting of liver basement membrane and extracts and hydrolysates thereof, and processed collagen from vertebrate non-submucosal sources, and further including added endothelial cells and at least one additional preselected, exogenous population of cells. The matrix composition is seeded with the endothelial cells and the preselected, exogenous population(s) of cells, and is used to repair diseased or damaged tissues. In accordance with the invention "damaged tissues" means tissues which are injured, lacerated, severed, or that have been surgically removed or are otherwise missing from the site in need of repair (e.g., congenital absence or deformity).

The matrix composition can be prepared from an extracellular matrix composition derived from liver basement membrane and extracts and hydrolysates thereof. However, the matrix composition can also be prepared from other engineered tissues to form, for example, an isolated basement membrane layer, or from a commercially available processed collagen composition, or a purified collagen composition. Exemplary of commercially available processed collagen compositions that may be used in accordance with the invention are MATRIGEL®, ALLODERM®, INTEGRA®, APPLIGRAF®, DERMAGRAFT®, and PERI-GUARD®. MATRIGEL® Basement Membrane Matrix (Becton Dickinson) is a tumor-derived basement membrane composition which is a soluble basement membrane extract of the Engelbreth-Holm-Swarm tumor, gelled to form a reconstituted basement membrane. ALLODERM® (Life Cell, Inc.) is a composition from cadaver dermis that has been processed to remove cells. INTEGRA® (Integra Life Sciences) is an acellular dermal composition of bovine collagen and chondroitin sulfate. APPLIGRAF® (Novartis) is a synthetic polylactic acid-containing composition that has been seeded with human fibroblasts and other cellular and non-cellular components, and DERMAGRAFT® is an allogenic dermal graft of human fibroblasts on a Vicryl mesh backbone. PERI-GUARD® (Bio-Vascular, Inc.) is a composition prepared from bovine pericardium which is chemically cross-linked. Purified and processed collagen can also be produced by techniques known in the art. (See, for example, U.S. Pat. Nos. 6,127,143, 5,814,328, 5,108,424, and 4,883,864.)

The endothelial cells for use in accordance with the invention can be derived from any type of endothelial cell population including macrovascular, microvascular, arterial, and venous endothelial cells. Either mature endothelial cells (e.g., harvested from an organ or a blood vessel) or endothelial cell precursors (e.g., progenitor cells or stem cells) can be used in accordance with the invention. Additionally, the endothelial cells can be harvested from a young or an old animal, but endothelial cells harvested from a young animal are preferred.

In one embodiment the additional preselected, exogenous population(s) of cells can comprise a population of non-keratinized or keratinized epithelial cells or a population of mesodermally derived cells selected from the group consisting of fibroblasts, smooth muscle cells, skeletal muscle cells, cardiac muscle cells, multi-potential progenitor cells, pericytes, osteogenic cells, or any other suitable cell type.

The additional preselected, exogenous population of cells, which is combined with the matrix composition and the endothelial cells, can be selected based on the cell type of the intended tissue to be repaired. For example, if skin is to be repaired, the preselected, exogenous population of cells can be non-keratinized epithelial cells or if cardiac tissue is to be repaired, the preselected, exogenous population of cells can be cardiac muscle cells. In another embodiment the matrix composition is seeded with autogenous cells isolated from the patient to be treated.

In one embodiment, the at least one additional preselected population of cells to be combined with the matrix composition and the endothelial cells includes smooth muscle cells and/or progenitor cells capable of differentiating into smooth muscle cells. Advantageously, the smooth muscle cells and/or smooth muscle progenitor cells can promote, along with the endothelial cells, the formation of vessels or vessel-like structures in the graft construct. In another embodiment, additional cell types can be added along with endothelial cells, smooth muscle cells, and/or smooth muscle cell progenitor cells.

In still another embodiment the at least one additional preselected, exogenous population of cells comprises a population of multi-potential progenitor cells. The matrix composition can induce the differentiation of these multi-potential progenitor cells into cells that assist in the repair of damaged tissues. Advantageously, the matrix composition seeded with a population of endothelial cells and a population of multi-potential progenitor cells can be implanted into a variety of different in vivo locations and the progenitor cells will differentiate into the appropriate cell type for the specific environment. For example, implantation of a composition comprising endothelial cells and multi-potential progenitor cells at the site of a tendon or a ligament will result in the graft construct remodeling into a tendon or a ligament.

The combination of the matrix composition, endothelial cells, and an additional preselected, exogenous population of cells provides a tissue graft construct that shows surprisingly enhanced vascularization in vitro and/or in vivo leading to improved wound healing capabilities and better restoration of tissue function compared to the use of either the matrix composition alone, in combination with endothelial cells alone, or in combination with cell types other than endothelial cells as therapeutic agents.

In various embodiments, the matrix composition can be seeded with the additional preselected population of cells after the matrix composition is seeded with the endothelial cells, the matrix composition can be seeded with the additional preselected population of cells before the matrix composition is seeded with the endothelial cells, or the matrix composition can be seeded with the endothelial cells and the additional preselected population of cells simultaneously or nearly simultaneously (see FIG. 1 for various exemplary embodiments).

In one such embodiment, the matrix composition can be seeded with endothelial cells and the endothelial cells can be cultured on the matrix composition prior to the implantation of the construct into the affected region for a time sufficient to induce the formation of vessels or vessel-like structures. The matrix composition can be seeded with the at least one additional preselected, exogenous population of cells after the matrix composition is seeded with the endothelial cells and at any time up to just prior to implantation of the graft construct in vivo. Accordingly, depending on the time allowed for culturing the preselected population of cells on the matrix composition prior to implantation of the graft construct, the additional preselected population of cells may or may not be expanded (i.e., allowed to progress through at least one cell division cycle) prior to implantation of the graft construct into the affected region.

Alternatively, the matrix composition can be seeded with the at least one additional preselected, exogenous population of cells after the matrix composition is seeded with the endothelial cells, and the endothelial cells can be cultured on the matrix composition to expand the endothelial cells without inducing the formation of vessels or vessel-like structures or components prior to implantation of the graft. In this embodiment, depending on the time allowed for culturing the preselected population of cells on the matrix composition prior to implantation of the graft construct, the additional preselected population of cells may or may not be expanded prior to implantation of the graft construct into the affected region.

In another embodiment, the matrix composition can be seeded with the at least one additional preselected, exogenous population of cells after the matrix composition is seeded with the endothelial cells and the matrix composition can be implanted soon thereafter without expansion of either the endothelial cells or the additional preselected, exogenous population of cells.

In an alternate embodiment, the matrix composition can be seeded with the additional preselected, exogenous population of cells and the preselected population of cells can be cultured on the matrix composition to expand (i.e., allow the cells to divide at least one time) the preselected cell population prior to implantation of the graft construct. In this embodiment, the matrix composition can be seeded with the endothelial cells after the matrix composition is seeded with the preselected population of cells and at any time up to just prior to implantation of the graft in vivo. Accordingly, depending on the time allowed for culturing the endothelial cells on the matrix composition prior to implantation of the graft, the endothelial cells may or may not be expanded prior to implantation of the graft construct into the affected region. If the endothelial cells are expanded, the expansion of the endothelial cells may or may not include the formation of vessels or vessel-like structures.

In another embodiment, the matrix composition can be seeded with the endothelial cells after the matrix composition is seeded with the at least one additional preselected, exogenous population of cells and the graft can be implanted soon thereafter without expansion of either the endothelial cells or the additional preselected, exogenous population of cells.

In yet another embodiment, the matrix composition can be seeded simultaneously or nearly simultaneously with the endothelial cells and the additional preselected, exogenous population of cells. In this embodiment, the endothelial cells and the additional preselected, exogenous population of cells can be cultured on the matrix composition to expand the two cell populations or the graft can be implanted without expansion of the two cell populations. If the endothelial cells are expanded, the expansion of the endothelial cells may or may not include the formation of vessels or vessel-like structures.

A matrix composition selected from the group consisting of liver basement membrane and extracts and hydrolysates thereof, and processed collagen from vertebrate non-submucosal sources, advantageously provides a physiological environment that supports the proliferation and differentiation of cells cultured in vitro on the matrix composition. Thus, cells can be seeded onto the matrix composition and can be cultured using standard cell culture techniques, as described below, known to those of ordinary skill in the art, to produce tissue grafts for implantation into a host in need thereof.

The ability of a matrix composition selected from the group consisting of liver basement membrane and extracts and hydrolysates thereof, and processed collagen from vertebrate non-submucosal sources, to provide a substrate that supports the growth of cells provides the opportunity to expand the population of endothelial cells and/or the additional preselected, exogenous population of cells prior to implantation into a host. If endothelial cells are expanded, such expansion can result in the formation of vessels or vessel-like structures (i.e., potential vascularization of the graft construct in vitro) prior to implantation improving the wound healing capabilities of the graft upon implantation of the graft construct. The formation of vessels or vessel-like structures prior to implantation of the graft construct or, alternatively, the expansion of endothelial cells prior to implantation of the graft construct improves the wound healing capabilities of the graft upon implantation such as by promoting differentiation and migration of cells growing on the surface of the graft construct and by promoting proliferation of cells within the graft construct.

In embodiments where the added endothelial cells, and the additional preselected, exogenous population of cells are cultured on the matrix composition prior to implantation, the cells are cultured on the matrix composition under conditions conducive to cell growth. The cultured cells can be in either direct or indirect contact (e.g., fluid communication) with the matrix composition. Conditions conducive to cell growth are environmental conditions, such as sterile technique, temperature (e.g., about 37° C.) and nutrient supply, that are considered optimal for cell growth under currently accepted procedures for tissue and cell culture. Although optimum culture conditions depend on the particular cell type, cell growth conditions are generally well known in the art.

Matrix compositions in accordance with the invention can be used in a variety of forms as a graft material and to culture endothelial cells and other cell types in vitro prior to implantation of the graft construct. These forms include a sheet-like configuration, a gel form, a fluidized composition (e.g., by comminuting or digesting the tissue), and an extract for addition to art-recognized cell/tissue culture media. The matrix composition or component(s) thereof can provide a surface for cell adhesion and/or can induce cell differentiation and/or proliferation. The matrix composition is preferably sterilized prior to use in tissue/cell culture applications, however, non-sterile compositions can be used if antibiotics are included in the cell culture media.

In one embodiment cells are seeded directly onto sheets of liver basement membrane tissue under conditions conducive to cell proliferation for culture of the cells prior to implantation of the graft construct. The porous nature of this tissue allows diffusion of cell nutrients throughout the matrix. Thus, cells can be seeded onto and cultured on either side of the liver basement membrane.

The endothelial cells and/or the additional preselected, exogenous population of cells seeded onto the matrix composition for culture prior to implantation of the graft construct can be grown in the presence of nutrients, including minerals, amino acids, sugars, peptides, proteins, or glycoproteins, such as laminin and fibronectin, and/or growth factors such as epidermal growth factor, vascular endothelial cell-derived growth factor, platelet-derived growth factor, platelet-derived growth factor-like molecules, transforming growth factor β, fibroblast growth factor, or another serum growth factor. In one embodiment fluidized or powder forms of the matrix composition can be used to supplement standard cell culture media to enhance the capacity for sustaining and inducing the proliferation of the cells in vitro and to induce remodeling in vivo. The cells can be grown on the matrix composition in the presence of commercially available cell culture liquid media (either serum-containing or serum-free).

In one embodiment, the at least one additional preselected population of cells to be combined with the matrix composition and the endothelial cells can be smooth muscle cells and/or progenitor cells capable of differentiating into smooth muscle cells to promote, along with the endothelial cells, the formation of vessels or vessel-like structures in the graft construct. It is known that treatment of smooth muscle cells with a heparinase can induce a phenotypic change characteristic of proliferating cells. Accordingly, in embodiments where the matrix composition is seeded with endothelial cells and at least one preselected, exogenous population of cells including a smooth muscle cell population and/or a smooth muscle cell progenitor cell population a heparinase can be included in the cell culture medium. For example, 4 units/ml of a heparinase from *Flavobaterium heparinum* can be included in the culture medium for a short interval (e.g., 6 hours) or can be present continually in the culture medium.

It is also known that smooth muscle cells that are seeded on a substrate as a subconfluent monolayer of cells undergo a phenotypic change associated with the capacity to divide. The phenotypic change is inhibited if the smooth muscle cells are co-cultured with a confluent monolayer of endothelial cells. Accordingly, in embodiments where the matrix composition is seeded with endothelial cells and at least one preselected, exogenous population of cells including a smooth muscle cell population and/or a smooth muscle cell progenitor cell population the added endothelial cells can be seeded onto the matrix composition so that the cells attach to the matrix composition as a subconfluent monolayer of cells. In another embodiment the endothelial cells, smooth muscle cells, and/or smooth muscle progenitor cells can be seeded onto the matrix composition so that the cells attach to the matrix composition as subconfluent monolayers of cells.

In one embodiment, the claimed compositions comprising the matrix composition, added endothelial cells, and an additional preselected, exogenous population of cells can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/alginate encapsulation process has been previously described by F. Lim and A. Sun (*Science*, Vol. 210, pp. 908-910). Indeed, liver basement membrane itself could be used advantageously to encapsulate the cells on a matrix in accordance with this invention for implantation as an artificial organ.

In one embodiment, a method is provided for enhancing the vascularization in vivo of a tissue graft construct. The method comprises the steps of seeding in vitro a matrix composition selected from the group consisting of liver basement membrane and extracts and hydrolysates thereof, and processed collagen from vertebrate non-submucosal sources, with a population of endothelial cells and at least one additional preselected, exogenous population of cells to form the graft construct, and implanting the graft construct into a vertebrate at a site in need of repair. In one embodiment of this method, the matrix composition can be seeded with endothelial cells and the endothelial cells can be cultured on the matrix composition prior to the implantation of the construct into the affected region for a time sufficient to induce the formation of vessels or vessel-like structures. The matrix composition can be seeded with the at least one additional preselected, exogenous population of cells after the graft is seeded with the endothelial cells and at any time up to just prior to implantation of the graft in vivo. Accordingly, depending on the time allowed for culturing the preselected population of cells on the matrix composition prior to implantation of the graft construct, the additional preselected population of cells may or may not be expanded prior to implantation of the graft construct into the affected region.

Alternatively, the matrix composition can be seeded with the at least one additional preselected, exogenous population of cells after the matrix composition is seeded with the endothelial cells, and the endothelial cells can be cultured on the matrix composition to expand the endothelial cells without inducing the formation of vessels or vessel-like structures prior to implantation of the graft. In this embodiment, depending on the time allowed for culturing the endothelial cells on the matrix composition prior to implantation of the graft construct, the additional preselected population of cells may or may not be expanded prior to implantation of the graft construct into the affected region.

In another embodiment, the matrix composition can be seeded with the at least one additional preselected, exogenous population of cells after the matrix composition is seeded with the endothelial cells and the graft can be implanted soon thereafter without expansion of either the endothelial cells or the additional preselected, exogenous population of cells.

In an alternate embodiment of this method, the matrix composition can be seeded with the additional preselected, exogenous population of cells and the preselected population of cells can be cultured on the matrix composition to expand the preselected cell population prior to implantation of the graft construct. In this embodiment, the matrix composition can be seeded with the endothelial cells after the matrix composition is seeded with the preselected population of cells and at any time up to just prior to implantation of the graft in vivo. Accordingly, depending on the time allowed for expansion of the endothelial cells by culturing the cells on the matrix composition prior to implantation of the graft, the endothelial cells may or may not be expanded prior to implantation of the graft construct into the affected region. If the endothelial cells are expanded, the expansion of the endothelial cells may or may not include the formation of vessels or vessel-like structures.

In another embodiment, the matrix composition can be seeded with the endothelial cells after the matrix composition is seeded with the at least one additional preselected, exogenous population of cells and the graft can be implanted soon thereafter without expansion of either the endothelial cells or the additional preselected, exogenous population of cells.

In yet another embodiment, the matrix composition can be seeded simultaneously or nearly simultaneously with the endothelial cells and the additional preselected, exogenous population of cells. In this embodiment, the endothelial cells and the additional preselected, exogenous population of cells can be cultured on the matrix composition to expand the two cell populations or the graft can be implanted without expansion of the two cell populations. If the endothelial cells are expanded, the expansion of the endothelial cells may or may not include the formation of vessels or vessel-like structures.

A vascularized tissue graft construct for use in repairing diseased or damaged tissues is also provided in accordance with the invention. The vascularized graft construct comprises a matrix composition selected from the group consisting of liver basement membrane and extracts and hydrolysates thereof, and processed collagen from vertebrate non-submucosal sources, and further includes added endothelial cells, and at least one additional preselected, exogenous population of cells wherein the endothelial cells have been cultured on the matrix composition for a time sufficient to form vessels or vessel-like structures in vitro.

In another embodiment, a method is provided for enhancing the vascularization in vivo of a tissue graft construct. The method comprises the steps of seeding a matrix composition selected from the group consisting of liver basement membrane and extracts and hydrolysates thereof, and processed collagen from vertebrate non-submucosal sources, in vitro with a population of endothelial cells and at least one additional preselected, exogenous population of cells, culturing in vitro the endothelial cells and the additional cell population on the matrix composition for a time sufficient to induce the formation of vessels or vessel-like structures, and implanting the graft construct into a vertebrate in a site in need of repair.

Matrix compositions in accordance with the invention can be seeded with initially small cell populations that can be expanded in vitro prior to implantation. Advantageously, seeding with endothelial cells can induce vascularization of the grafts in vitro upon culturing the endothelial cells in vitro on the matrix composition. The matrix composition can be further seeded with smooth muscle cells or smooth muscle cell progenitor cells or another cell type, such as fibroblasts, to promote vascularization.

In this embodiment, the matrix composition is seeded with endothelial cells and the endothelial cells are cultured on the matrix composition prior to the implantation of the construct into the affected region for a time sufficient to induce the formation of vessels or vessel-like structures. The matrix composition can be seeded with the at least one additional preselected, exogenous population of cells after the matrix composition is seeded with the endothelial cells and at any time up to just prior to implantation of the graft in vivo. Accordingly, depending on the time allowed for culturing the preselected population of cells on the matrix composition prior to implantation of the graft, the additional preselected population of cells may or may not be expanded prior to implantation of the graft construct into the affected region.

In an alternate embodiment, the matrix composition can be seeded with the additional preselected, exogenous population of cells and the preselected population of cells can be cultured on the matrix composition to expand the preselected cell population prior to implantation of the graft construct. In this embodiment, the matrix composition is seeded with endothelial cells after the matrix composition is seeded with the preselected population of cells. In this embodiment, the endothelial cells are cultured on the matrix composition for a time sufficient to allow for expansion of the endothelial cells to form vessel or vessel-like structures prior to implantation of the graft construct into the affected region.

In another embodiment, the matrix composition can be seeded with the endothelial cells and the additional preselected, exogenous population of cells simultaneously or nearly simultaneously. In this embodiment, the additional preselected, exogenous population of cells and the endothelial cells are cultured on the matrix composition to expand the two cell populations prior to implantation of the graft.

A method of preparing a tissue graft construct for use in repairing diseased or damaged tissues is also provided. The method comprises the step of seeding in vitro a matrix composition selected from the group consisting of liver basement membrane and extracts and hydrolysates thereof, and processed collagen from vertebrate non-submucosal sources, with a population of endothelial cells, and at least one additional preselected, exogenous population of cells to form the graft construct. The method can further comprise the step of culturing the endothelial cells on the matrix composition for a time sufficient to induce the formation of vessels or vessel-like structures prior to the implantation of the graft construct into the affected region.

The matrix composition can be made from liver basement membrane (LBM) prepared by separating the LBM from the natively associated cellular components of liver tissue of a vertebrate. The preparative techniques described below provide an extracellular matrix composition consisting essentially of LBM substantially free of any cellular components.

Basement membrane for use in the matrix composition in accordance with the invention is typically prepared from liver tissue harvested from animals raised for meat production, including, for example, pigs, cattle and sheep or other vertebrates. Thus, there is an inexpensive commercial source of liver tissue for use in preparation of the compositions used in accordance with the present invention. The LBM composition does not induce an adverse host immune response when the composition is used in the delivery systems of the present invention.

To prepare the acellular LBM composition, the liver tissue is treated with a cell dissociation solution for a period of time sufficient to release the cellular components of the liver tissue from the extracellular components without substantial disruption of the extracellular components, and the cellular components are separated from the extracellular components. Typically the cell dissociation solution comprises a chaotropic agent or an enzyme or both.

The first step in preparing LBM is to slice a segment of liver tissue into pieces (e.g., strips or sheets) to increase the surface area-to-volume ratio of the liver tissue. The liver tissue may be sliced into a series of sheets each having a thickness of about 50 to about 500 microns, more preferably about 250 to about 300 microns. Freshly harvested liver tissue can be sliced using a standard meat slicer, or the tissue can be frozen and sliced with a cryomicrotone. The thin pieces of liver tissue are then treated with a solution that releases component liver cells from the associated extracellular basement membrane matrix.

The liver tissue can be treated with a solution comprising an enzyme, for example, a protease, such as trypsin or pepsin. Because of the collagenous structure of the LBM and the desire to minimize degradation of the membrane structure during cell dissociation, collagen specific enzyme activity should be minimized in the enzyme solutions used for cell-dissociation. In addition, the liver tissue is typically also treated with a calcium chelating agent or chaotropic agent (e.g., Triton X-100). Thus, the liver tissue is treated by suspending slices or strips of the tissue in a cell-dissociation solution containing enzyme(s) and chaotropic agent(s). However, cell dissociation can also be conducted using a calcium chelating agent or chaotropic agent in the absence of an enzymatic treatment of the tissue.

Cell dissociation can be carried out by suspending, with agitation, liver tissue slices in a solution containing about 0.05 to about 2%, more typically about 0.1 to about 1% by weight of protease, optionally containing a chaotropic agent or a calcium chelating agent in an amount effective to optimize release and separation of cells from the basement membrane without substantial degradation of the membrane matrix.

After contacting the liver tissue with the cell-dissociation solution for a sufficient time to release all cells from the matrix, the resulting LBM is rinsed one or more times with saline and optionally stored in a frozen hydrated state or a partially dehydrated state until used. Cell dissociation may require several treatments to release substantially all cells from the basement membrane. The resulting LBM preparation can be further treated to remove or inhibit any residual enzyme activity. For example, the resulting basement membrane can be heated or treated with one or more protease inhibitors.

In another embodiment, LBM can be prepared as follows. Freshly harvested liver tissue can be sliced using a standard meat slicer into a series of sheets each having a thickness of about 50 to about 2000 microns, or the tissue can be frozen and sliced with a meat slicer or cryomicrotone. The liver tissue is then rinsed one or more times, such as with deionized water, saline, or a buffered solution and optionally stored in a frozen hydrated state or a partially dehydrated state until used. For example, the liver sheets or strips could be rinsed three times for 30 minutes each with deionized water, saline, or a buffer. The rinse solution can then be strained from the liver slices, for example, using a sieve, and each liver slice can be massaged on a screen or ultrasound can be used to hasten lysis of hepatocytes and to mechanically dissociate hepatocytes and hepatocyte cell fragments from the liver basement membrane.

The thin slices of liver tissue are then contacted with a solution containing a protease, such as trypsin, that releases liver cells and other components from the associated extracellular basement membrane matrix. Because of the collagenous structure of the liver basement membrane and the desire to minimize degradation of the membrane structure during cell dissociation, collagen specific enzyme activity should be minimized in the enzyme solutions used in the protease digestion step. The liver tissue is typically also contacted with a calcium chelating agent such as EDTA concurrently with the protease treatment.

In one preferred embodiment the protease digestion step is carried out by contacting liver tissue slices with a solution, optionally with agitation, containing 0.02% of trypsin by weight and containing EDTA at a concentration of about 0.05% by weight. The protease digestion step is preferably carried out with heating, typically at about 37° C. The rinsing and mechanical dissociation steps described above may be repeated after the protease digestion step.

The liver slices are then contacted with a solution containing a non-denaturing detergent. This step is preferably carried out at room temperature, and optionally with agitation. The non-denaturing detergent is preferably 3% Triton X-100. The rinsing steps described above are repeated after contacting the liver slices with the non-denaturing detergent to remove most, if not all, of the non-denaturing detergent. The mechanical dissociation steps may be repeated as needed.

After treatment with the non-denaturing detergent, the liver slices are contacted with a solution containing a denaturing detergent. This step is preferably carried out at room temperature and optionally with agitation. The denaturing detergent is preferably 4% deoxycholate. The LBM is then thoroughly rinsed as described above to remove as much residual detergent as possible and the LBM can be stored (e.g., in deionized water at 4° C.) until further use or can be used immediately following the purification procedure.

After preparation, LBM can be fluidized in a manner similar to the preparation of fluidized submucosa, as described in U.S. Pat. No. 5,275,826 the disclosure of which is expressly incorporated herein by reference. LBM is comminuted by tearing, cutting, grinding, shearing and the like. Grinding the liver basement membrane in a frozen or freeze-dried state is preferred although good results can be obtained as well by subjecting a suspension of liver basement membrane to treatment in a high speed (high shear) blender and dewatering, if necessary, by centrifuging and decanting excess water. Additionally, the comminuted fluidized tissue can be solubilized by enzymatic digestion with a protease, for example a collagenase and or other appropriate enzyme, such as glycanase, or other enzyme that disrupts the matrix structural components, for a period of time sufficient to solubilize the tissue and form a substantially homogeneous solution.

The viscosity of fluidized LBM for use in transdermal or transmucosal drug delivery in accordance with this invention can be manipulated by controlling the concentration of the LBM component and the degree of hydration. The viscosity can be adjusted to a range of about 2 to about 300,000 cps at 25° C. Higher viscosity formulations, for example, gels, can be prepared from the LBM digest solutions by dialyzing the digested material and then adjusting the pH of such solutions to about 5.0 to about 9.0.

LBM can also be prepared in the form of an extract. Briefly, LBM can be suspended in an extraction buffer with agitation for about 24 hours at 4° C. The extraction mixture can be centrifuged at 12,000×g for about 30 minutes at 4° C. and the supernatant collected. The insoluble material can then be washed with the extraction buffer and the centrifugation step repeated and the wash combined with the original supernatant. The supernatant can be dialyzed (MWCO about 3500) extensively against deionized water and the dialyzate centrifuged at 12,000×g. The supernatant can be used immediately or lyophilized for storage.

Powder forms of LBM can also be used in accordance with the invention. Powder forms are prepared by pulverizing the tissue under liquid nitrogen to produce particles ranging in size from 0.1 to 1 $mm^2$. The particulate composition is then lyophilized overnight and sterilized to form a solid substantially anhydrous particulate composite. Alternatively, a powder form of LBM can be formed from fluidized LBM by drying the suspensions or solutions of comminuted LBM. LBM in powder form or in fluidized form or in the form of a gel or an extract can be used to culture endothelial cells and the preselected cell population in vitro prior to implantation of the graft construct in accordance with the invention.

MATRIGEL®, ALLODERM®, and INTEGRA®, DERMAGRAFT®, PERI-GUARD®, and APPLIGRAF® are commercially available processed collagen compositions. Purified and processed collagen compositions can also be prepared by protocols known in the art. For example, see U.S. Pat. Nos. 6,127,143, 5,814,328, 5,108,424, and 4,883,864 incorporated herein by reference.

EXAMPLE 1

Preparation of Liver Basement Membrane Compositions 2 mM EDTA Buffered Chaotropic Solution Used in the Experiment

| 140 mM | NaCl |
|---|---|
| 5 mM | KCl |
| 0.8 mM | $MgSO_4$ |
| 0.4 mM | $KH_2PO_4$ |
| 2 mM | EDTA |
| 25 mM | $NaHCO_3$ |

Procedure:

Preparation of Liver Slices:

Liver frozen at −70° C. was sliced with a cryomicrotone to a thickness of about 50μ. The slices of liver tissue were then subjected to enzymatic treatment (0.1% trypsin) with the chaotropic solution (2 mM EDTA) described above.

Liver slices were placed in five 50 ml tubes, each of which contained 25 ml of the buffered enzyme treatment solution. The liver tissue was incubated at 37° C. in water bath with gentle shaking for 1 hour. The liver slices were washed twice with PBS with agitation/shaking for 1 hour at room temperature. The above enzymatic treatment steps were repeated three times. Frozen tissue was sliced into 1 cm cubes, pulverized under liquid nitrogen with an industrial blender to particles less than 2 mm2 and stored at −80° C. prior to use.

Preparation of Extracts of Liver Basement Membrane7

Extraction buffers used for these studies included 4 M guanidine and 2M urea each prepared in 50 mM Tris-HCl, pH 7.4. The powder form of liver basement membrane was suspended in the relevant extraction buffer (25% w/v) containing phenylmethyl sulphonyl fluoride, N-ethylmaleimide, and benzamidine (protease inhibitors) each at 1 mM and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000×g to remove any insoluble material and the supernatant was used immediately or lyophilized for storage.

Preparation of Fluidized Liver Basement Membrane

Partial digestion of the pulverized material described above was performed by adding 5 g of powdered tissue to a 100 ml solution containing 0.1% pepsin in 0.5 M acetic acid and digesting for 72 hours at 4° C. Following partial digestion, the suspension was centrifuged at 12,000 rpm for 20 minutes at 4° C. and the insoluble pellet discarded. The supernatant was dialyzed against several changes of 0.01 M acetic acid at 4° C. (MWCO 3500). The solution was sterilized by adding chloroform (5 ml chloroform to 900 ml of 0.01 M acetic acid) to the LBM hydrolysate. Dialysis of the LBM was continued with two additional changes of sterile 0.01 M acetic acid to eliminate the chloroform. The contents of the dialysis bag were then transferred aseptically to a sterile container. The resultant fluidized composition was stored at 4° C.

Preparation of Liver Basement Membrane Gel Compositions

To prepare the gel form of LBM, 8 mls of fluidized LBM was mixed with 1.2 ml 10×PBS buffer (10× phosphate buffered saline containing 5 mg/L phenol red); 0.04 N HCl (approx 1.6 ml) was added to adjust the pH to between 6.6 and 7.4 and then 0.05 N NaOH (approx. 1.2 ml) was added to shift the pH to >8. The final volume was adjusted to 12 ml with water.

EXAMPLE 2

Growth of Endothelial Cells

Liver basement membrane is prepared as described above. Following sterilization via various techniques (gamma irradiation, peracetic acid, etc.), the tissue is clamped within a polypropylene frame to create a flat surface area (50 mm$^2$) for cell growth. The frame is submerged in tissue culture medium to allow access of medium nutrients to both surfaces of the liver basement membrane. Endothelial cells and smooth muscle cells are seeded (at 3×10$^4$ cells/tissue section) on the liver basement membrane and then placed in a 5% $CO_2$, 95% air incubator at 37° C. Following various periods of time, the seeded liver basement membrane is fixed in 10% neutral buffered formalin, embedded in paraffin, and sectioned (6 um). Various histological and immunohistochemical staining procedures are done to determine the cell growth characteristics. Vessels or vessel-like structures are observed using these procedures.

The invention claimed is:

1. A method for enhancing the vascularization in vivo of a tissue graft construct, said method comprising the steps of:
    seeding in vitro a matrix composition selected from the group consisting of liver basement membrane and extracts and hydrolysates thereof, and processed collagen from vertebrate non-submucosal sources, with a population of endothelial cells and at least one additional preselected, exogenous population of cells to form the graft construct wherein said additional population of cells enhances the initiation of vascularization of said graft construct; and
    implanting said graft construct into a vertebrate at a site in need of repair.

2. The method of claim 1 wherein the at least one additional cell population comprises a population of cells selected from the group consisting of keratinized epithelial cells, non-keratinized epithelial cells, and mesodermally derived cells.

3. The method of claim 1 wherein the at least one additional cell population comprises a population of smooth muscle cells.

4. The method of claim 1 wherein the at least one additional cell population comprises a population of smooth muscle cell progenitor cells.

5. The method of claim 1 wherein the at least one additional cell population comprises fibroblasts.

6. The method of claim 1 wherein the graft construct further comprises a heparinase.

7. The method of claim 1 wherein the graft construct further comprises a growth factor selected from the group consisting of vascular endothelial cell-derived growth factor, platelet-derived growth factor, a platelet-derived growth factor-like molecule, transforming growth factor β, and a serum growth factor.

8. The method of claim 1 further comprising the step of culturing said endothelial cells on said matrix composition for a time sufficient to form vessels or vessel-like structures in vitro before implanting said graft construct into the vertebrate.

9. The method of claim 8 wherein the matrix composition is seeded with the additional preselected population of cells after the matrix composition is seeded with the endothelial cells.

10. The method of claim 8 wherein the matrix composition is seeded with the endothelial cells after the matrix composition is seeded with the additional preselected population of cells.

11. The method of claim 8 wherein the matrix composition is seeded simultaneously with the endothelial cells and the additional preselected population of cells.

12. The method of claim 11 wherein the additional preselected population of cells is expanded prior to implanting the graft construct.

13. The method of claim 11 wherein the additional preselected population of cells is not expanded prior to implanting the graft construct.

14. The method of claim 1 wherein the matrix composition is seeded with the additional preselected population of cells after the matrix composition is seeded with the endothelial cells.

15. The method of claim 14 wherein neither the endothelial cells nor the additional preselected population of cells is expanded prior to implanting the graft construct.

16. The method of claim 14 further comprising the steps of culturing the endothelial cells on the matrix composition for a time sufficient to expand the endothelial cells without forming vessels or vessel-like structures in vitro and culturing the additional preselected population of cells on the matrix composition for a time sufficient to expand the additional preselected population of cells before implanting the graft construct into the vertebrate.

17. The method of claim 14 further comprising the step of culturing the endothelial cells on the matrix composition for a time sufficient to expand the endothelial cells without forming vessels or vessel-like structures in vitro.

18. The method of claim 17 wherein the additional preselected population of cells is not expanded prior to implanting the graft construct.

19. The method of claim 14 further comprising the step of culturing the additional preselected population of cells on the matrix composition for a time sufficient to expand the preselected population of cells prior to implanting the graft construct.

20. The method of claim 19 wherein the endothelial cells are not expanded prior to implanting the graft construct.

21. The method of claim 1 wherein the matrix composition is seeded with the endothelial cells after the matrix composition is seeded with the additional preselected population of cells.

22. The method of claim 1 wherein the matrix composition is seeded with the endothelial cells and the additional preselected population of cells simultaneously or nearly simultaneously.

* * * * *

UNITED STATES PATENT AND TRADEMARK OFFICE
CERTIFICATE OF CORRECTION

| | | |
|---|---|---|
| PATENT NO. | : 8,084,048 B2 | Page 1 of 1 |
| APPLICATION NO. | : 12/557176 | |
| DATED | : December 27, 2011 | |
| INVENTOR(S) | : Stephen F. Badylak | |

It is certified that error appears in the above-identified patent and that said Letters Patent is hereby corrected as shown below:

In column 1, lines 14 to 16, please replace the text "This invention was made with government support under Grant No. GM60691-01 awarded by the National Institutes of Health. The government has certain rights in the invention." with the text -- This invention was made with government support under Grant No. GM606911 awarded by the National Institutes of Health. The government has certain rights in the invention. --

Signed and Sealed this
Second Day of October, 2012

David J. Kappos
*Director of the United States Patent and Trademark Office*